(12) United States Patent
Basa et al.

(10) Patent No.: US 10,226,414 B2
(45) Date of Patent: *Mar. 12, 2019

(54) DENTIFRICE COMPOSITIONS WITH IMPROVED FLUORIDE STABILITY

(71) Applicant: The Procter & Gamble Company, Cincinnanti, OH (US)

(72) Inventors: Swapna Basa, Beijing (CN); Ross Strand, Singapore (SG); Hongmei Yang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,831

(22) Filed: Aug. 20, 2015

(65) Prior Publication Data
US 2016/0030326 A1    Feb. 4, 2016

(30) Foreign Application Priority Data

May 15, 2014 (CN) .............................. 2014/077536
May 28, 2015 (CN) .............................. 2015/077634

(51) Int. Cl.
| A61K 8/19 | (2006.01) |
| A61K 8/21 | (2006.01) |
| A61Q 11/00 | (2006.01) |
| A61K 8/73 | (2006.01) |
| A61K 8/24 | (2006.01) |
| A61K 8/34 | (2006.01) |
| A61K 8/46 | (2006.01) |
| A61K 8/86 | (2006.01) |

(52) U.S. Cl.
CPC ................. *A61K 8/73* (2013.01); *A61K 8/19* (2013.01); *A61K 8/21* (2013.01); *A61K 8/24* (2013.01); *A61K 8/463* (2013.01); *A61K 8/86* (2013.01); *A61Q 11/00* (2013.01); *A61K 2800/28* (2013.01)

(58) Field of Classification Search
CPC . A61K 33/06; A61K 8/19; A61K 8/73; A61K 8/21; A61K 8/24; A61K 8/86; A61K 8/463; A61Q 11/00
See application file for complete search history.

(56) References Cited

U.S. PATENT DOCUMENTS

| 3,119,743 | A | 1/1964 | Ericsson |
| 4,046,872 | A | 9/1977 | Mitchell et al. |
| 4,283,385 | A | 8/1981 | Dhabhar et al. |
| 4,565,691 | A | 1/1986 | Jackson |
| 4,678,662 | A | 7/1987 | Chan |
| 4,701,319 | A | 10/1987 | Woo |
| 4,828,849 | A | 5/1989 | Lynch et al. |
| 5,939,052 | A | 8/1999 | White, Jr. et al. |
| 6,106,811 | A | 8/2000 | Gibbs |
| 6,159,446 | A | 12/2000 | Randive et al. |
| 6,696,045 | B2 | 2/2004 | Yue et al. |
| 6,759,876 | B2 | 7/2004 | Inoue et al. |
| 6,855,325 | B1 | 2/2005 | Yvin et al. |
| 7,648,363 | B2 | 1/2010 | Oniki et al. |
| 8,007,771 | B2 | 8/2011 | Ramji et al. |
| 2002/0001569 | A1 | 1/2002 | Dromard et al. |
| 2003/0072721 | A1 | 4/2003 | Riley et al. |
| 2003/0095931 | A1 | 5/2003 | Stier |
| 2004/0120902 | A1 | 6/2004 | Wernett et al. |
| 2004/0131560 | A1 | 7/2004 | Corcoran et al. |
| 2006/0134020 | A1 | 6/2006 | Robinson et al. |
| 2006/0159631 | A1 | 7/2006 | Buch et al. |
| 2007/0166243 | A1* | 7/2007 | Yoshida ................. A61Q 11/00 424/49 |
| 2007/0231278 | A1 | 10/2007 | Lee et al. |
| 2008/0230298 | A1 | 9/2008 | Buch et al. |
| 2009/0136584 | A1 | 5/2009 | Hosoya et al. |
| 2009/0202453 | A1* | 8/2009 | Waterfield ............... A61K 8/19 424/52 |
| 2009/0269287 | A1 | 10/2009 | Berta |
| 2010/0086498 | A1 | 4/2010 | Haught et al. |
| 2012/0189561 | A1 | 7/2012 | Randive et al. |
| 2013/0064779 | A1 | 3/2013 | Yamane et al. |
| 2013/0280182 | A1 | 10/2013 | Burgess et al. |
| 2013/0344120 | A1 | 12/2013 | Scott et al. |
| 2014/0314690 | A1 | 10/2014 | Fisher et al. |

FOREIGN PATENT DOCUMENTS

| CN | 101690699 | 4/2010 |
| CN | 102283795 A | 12/2011 |
| CN | 102283794 B | 7/2013 |
| EP | 2057978 A1 | 5/2009 |
| KR | 2002/0054045 A | 7/2002 |
| KR | 2012/0042399 A | 5/2012 |
| WO | WO1998022079 A1 | 5/1998 |

(Continued)

OTHER PUBLICATIONS

Pearce, et al. "The Effect of pH, Temperature and Plaque Thickness on the Hydrolysis of Monofluorophosphate in Experimental Dental Plaque", Caries Research, vol. 37, pp. 178-184, Feb. 1, 2003.
International Search Report and Written Opinion for PCT/CN2014/077427 dated Feb. 17, 2016.
International Search Report and Written Opinion for PCT/CN2014/077536 dated May 15, 2014.
International Search Report and Written Opinion for PCT/CN2015/077634 dated Jul. 22, 2015.

(Continued)

*Primary Examiner* — Lezah Roberts
(74) *Attorney, Agent, or Firm* — Parker D. McCrary; James E. Oehlenschlager

(57) ABSTRACT

Soluble fluoride ion stability is increased in certain dentifrice formulations with the use of carrageenan, particularly under alkaline pH conditions.

20 Claims, 2 Drawing Sheets

(56) References Cited

FOREIGN PATENT DOCUMENTS

| WO | WO200706001 A2 | 7/2007 |
|---|---|---|
| WO | WO 2007/122146 A1 | 11/2007 |
| WO | WO2008005548 A2 | 1/2008 |
| WO | WO2008041055 A1 | 4/2008 |
| WO | WO2010114546 A1 | 10/2010 |
| WO | WO2011031807 A2 | 3/2011 |
| WO | WO2011157497 A1 | 12/2011 |
| WO | WO2013034421 A2 | 3/2013 |
| WO | WO2013094312 A1 | 6/2013 |
| WO | WO2015094152 A1 | 6/2015 |
| WO | WO2015094154 A1 | 6/2015 |

OTHER PUBLICATIONS

Supplementary International Ssearch Report and Written Opinion for PCT/CN2015/077634 dated Feb. 26, 2016.
International Search Report and Written Opinion for PCT/CN2014/077527 dated Feb. 10, 2015.
Supplementary European Search Report (EP 15793035) dated Oct. 20, 2017.
All Office Actions, U.S. Appl. No. 14/633,256, filed Feb. 27, 2015.
All Office Actions, U.S. Appl. No. 14/633,389, filed Feb. 27, 2015.
All Office Actions, U.S. Appl. No. 14/635,196, filed Mar. 2, 2015.
All Office Actions, U.S. Appl. No. 15/294,855, filed Oct. 17, 2016.
All Office Actions, U.S. Appl. No. 14/634,969, filed Mar. 2, 2015.
All Office Actions, U.S. Appl. No. 14/635,234, filed Mar. 2, 2015.
All Office Actions, U.S. Appl. No. 14/700,182, filed Apr. 30, 2015.
All Office Actions, U.S. Appl. No. 14/830,815, filed Aug. 20, 2015.
All Office Actions, U.S. Appl. No. 14/634,993, filed Mar. 19, 2015.
All Office Actions, U.S. Appl. No. 14/634,949, filed Apr. 14, 2015.
All Office Actions, U.S. Pat. No. 9,364,419 filed Apr. 9, 2015.
All Office Actions, U.S. Appl. No. 15/150,486, filed May 10, 2016.
All Office Actions, U.S. Appl. No. 14/682,141, filed Apr. 9, 2015.
All Office Actions, U.S. Appl. No. 14/682,146, filed Apr. 9, 2015.
All Office Actions, U.S. Appl. No. 14/700,196, filed Apr. 30, 2015.
All Office Actions, U.S. Appl. No. 14/830,839, filed Aug. 20, 2015.
All Office Actions, U.S. Appl. No. 14/736,352, filed Jun. 11, 2015.

* cited by examiner

| Components: (Wt%) | Ex 1 | Ex 2 | Ex 3 | Ex 4 | Ex 5 | Ex 6 | Ex 7 | Ex 8 |
|---|---|---|---|---|---|---|---|---|
| Control | E | - | - | - | - | - | - | - |
| Tetra Sodium Pyrophosphate | 0 | 0 | 0 | 0 | 0 | 0 | 0 | 0 |
| Sorbitol | 17 | 17 | 17 | 17 | 17 | 0 | 0 | 0 |
| Iota-Carrageenan | 0 | 0.4 | 0.8 | 1.3 | 2 | 1 | 2 | 3 |
| Kappa-Carrageenan | - | - | - | - | - | - | - | - |
| Lambda-Carrageenan | - | - | - | - | - | - | - | - |
| Sodium Caboxy-methyl Cellulose | 1.3 | 0.9 | 0.5 | 0 | 0 | 1.3 | 1.3 | 0 |
| Thickening Silica | 3 | 3 | 3 | 3 | 0 | 0 | 0 | 0 |
| Sodium Saccharine | 0.25 | 0.25 | 0.25 | 0.25 | 0.25 | 0.25 | 0.25 | 0.25 |
| Sodium Monofluorophosphate | 1.1 | 1.1 | 1.1 | 1.1 | 1.1 | 1.1 | 1.1 | 1.1 |
| Sodium Monophosphate | 0.08 | 0.08 | 0.08 | 0.08 | 0.08 | 0.08 | 0.08 | 0.08 |
| Sodium Triphosphate | 0.42 | 0.42 | 0.42 | 0.42 | 0.42 | 0.42 | 0.42 | 0.42 |
| Calcium Carbonate | 42 | 42 | 42 | 42 | 42 | 42 | 42 | 42 |
| Sodium Lauryl Sulfate | 2.1 | 2.1 | 2.1 | 2.1 | 2.1 | 1.1 | 1.1 | 1.1 |
| Flavor | 1 | 1 | 1 | 1 | 1 | 0.85 | 0.85 | 0.85 |
| Water | 31.75 | 31.75 | 31.75 | 31.75 | 34.05 | 51.9 | 50.9 | 51.2 |
| Total: | 100 | 100 | 100 | 100 | 100 | 100 | 100 | 100 |
| pH: | 9.5 | 9.0 | 9.1 | 9.05 | 9.6 | 9.5 | 9.5 | 9.5 |

Fig. 1A

| Components: (Wt%) | Ex 9 | Ex 10 | Ex 11 | Ex 12 | Ex 13 | Ex 14 | Ex 15 |
|---|---|---|---|---|---|---|---|
| Control | - | - | - | A | B | C | D |
| Tetra Sodium Pyrophosphate | 0 | 0 | 0 | 0 | 0.5 | 0 | 0 |
| Sorbitol | 0 | 0 | 0 | 0 | 0 | 0 | 0 |
| Iota-Carrageenan | - | - | 1.414 | 0 | 0 | 2 | 1.4 |
| Kappa-Carrageenan | 2 | - | 0 | 0 | 0 | - | - |
| Lambda-Carrageenan | - | 2 | 0 | 0 | 0 | - | - |
| Sodium Caboxy-methyl Cellulose | 1.30 | 1.3 | 0.9 | 1.32 | 1.32 | 0.4 | 0.4 |
| Thickening Silica | 0.00 | 0 | 2.6 | 3.6 | 3 | 3 | 0.5 |
| Sodium Saccharine | 0.25 | 0.25 | 0.58 | 0.58 | 0.58 | 0.48 | 0.48 |
| Sodium Monofluorophosphate | 1.10 | 1.1 | 1.1 | 1.1 | 1.1 | 0.8 | 0.8 |
| Sodium Monophosphate | 0.08 | 0.08 | 0.08 | 0.08 | 0.08 | 0 | 0 |
| Sodium Triphosphate | 0.42 | 0.42 | 0.42 | 0.42 | 0.42 | 0 | 0 |
| Calcium Carbonate | 42 | 42 | 42 | 42 | 42 | 25 | 42 |
| Sodium Lauryl Sulfate | 1.10 | 1.1 | 1.1 | 1.1 | 1.1 | 2 | 2 |
| Flavor | 0.85 | 0.85 | 0.85 | 0.85 | 0.85 | 1 | 1 |
| Water | 50.9 | 50.9 | 48.96 | 48.95 | 49.05 | 65.32 | 51.42 |
| Total: | 100 | 100 | 100 | 100 | 100 | 100 | 100 |
| pH: | 9.5 | 9.5 | 9.4 | 9.2 | 9.4 | 7.8 | 8.3 |

Fig. 1B

DENTIFRICE COMPOSITIONS WITH IMPROVED FLUORIDE STABILITY

CROSS REFERENCES TO RELATED APPLICATIONS

This application claims the benefit of Application Serial No. CN2015/077634 filed Apr. 28, 2015; and Application Serial No. CN2014/077529 filed May 15, 2014.

FIELD OF THE INVENTION

The present invention relates to dentifrice composition having a fluoride ion source.

BACKGROUND OF THE INVENTION

Dentifrice compositions are well known for dental and oral hygiene care. High water (e.g., >45 wt %) and high carbonate (e.g., >25 wt %) formulation chassis are a cost effective for many markets and consumers. The use of linear sulfated polysaccharide (e.g., carrageenan) has been reported in dentifrice compositions as a thickening agent. However, this formulation chassis sometimes has fluoride ion stability issues that often exacerbated when there are high temperatures and/or long distribution times such as in some developing markets. Fluoride, and its associated benefits, is critical for a user's experience and product acceptance. There is a need to provide dentifrice formulations having improved fluoride ion stability.

SUMMARY OF THE INVENTION

The present invention is based, in part, on the surprising observation that soluble fluoride ion stability is increased in high water and high carbonate dentifrice formulations with the use of carrageenan. Furthermore, this fluoride ion stability effect is further enhanced under pH conditions that are greater than pH 8, preferably greater than pH 8.0. Yet still further, of the carrageenans, Lambda-carrageenan appears to be the best performing one for fluoride ion stability.

Accordingly, an advantage of the present invention is soluble fluoride stability over time. The advantages are observed in accelerated high temperature (e.g., 60° C. for 6 weeks) as well as long term ambient conditions (e.g., 30° C. for 1 year).

One aspect of the invention provides for dentifrice composition comprising: (a) 45% to 75% water, preferably 50% to 60% water, by weight of the composition; (b) 25% to 50%, preferably 27% to 47%, preferably 27% to 37% of a calcium-containing abrasive by weight of the composition, preferably wherein the calcium-containing abrasive is calcium carbonate; (c) 0.0025% to 2%, preferably from 0.5% to 1.5% of a fluoride ion source by weight of the composition, preferably wherein the fluoride ion source is sodium monofluorophosphate; (d) 0.01%% to 7%, preferably from 0.1% to 6% of a linear sulfated polysaccharide by weight of the composition, preferably wherein the linear sulfated polysaccharide is a carrageenan; and (e) pH greater than 8.0, preferably greater than 8.5, more preferably at or greater than pH 9.

Another aspect of the invention provides a dentifrice composition comprising: (a) 45% to 75%, preferably 50% to 60% water by weight of the composition; (b) 25% to 50%, preferably 27% to 47%, preferably 27% to 37% of a calcium-containing abrasive by weight of the composition, preferably wherein the calcium-containing abrasive comprises calcium carbonate; (c) 0.0025% to 2%, preferably from 0.5% to 1.5% of a fluoride ion source by weight of the composition, preferably the fluoride ion source comprises sodium monofluorophosphate; and (d) 0.01%% to 7%, preferably from 0.1% to 6% of a Lambda-carrageenan by weight of the composition.

Yet another aspect of the invention provides a method of treating tooth enamel comprising the step of brushing teeth with an oral care composition of the preceding claims.

While the specification concludes with claims that particularly point out and distinctly claim the invention, it is believed the present invention will be better understood from the following description.

BRIEF DESCRIPTION OF THE DRAWINGS

FIGS. 1A and 1B describe dentifrice formulations of Examples 1-15, wherein Examples 1, 12, 13, 14, and 15 are control formulations.

DETAILED DESCRIPTION OF THE INVENTION

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of" The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Water

The compositions of the present invention comprise herein from 45% to 75%, by weight of the composition of water. In one embodiment, the composition includes from 40% to 70%, alternatively from 45% to 65%, alternatively from 40% to 60%, alternatively from 50% to 70%, alternatively from 50% to 60%, alternatively from 45% to 55%, alternatively from 55% to 65%, alternatively from 50% to 60%, alternatively about 55%, alternatively combinations thereof, of water by weight of the composition. The water may be added to the formulation and/or may come into the composition from the inclusion of other ingredients. Preferably the water is USP water.

Calcium-Containing Abrasive

The compositions of the present invention comprise from 25% to 50% by weight of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In preferred embodiment, the composition comprises from 25% to 60%, more preferably from 25% to 50%, even more preferably from 25% to 40%, yet even more preferably from 26% to 39%, alternatively from 27% to 47%, alternatively from 27% to 37%, alternatively from 30% to 35%, alternatively from 30% to 34%, alternatively combinations thereof, of a calcium-containing abrasive by weight of the composition.

In yet still a further preferred composition contains calcium-containing abrasive at the previously indicated weight percentage, wherein the calcium-containing abrasive is a calcium carbonate, and wherein the calcium carbonate has: a D50 particle size range from 2 microns to 7 microns, preferably from 3 microns to 6 microns, more preferably from 3.4 microns to 5.8 microns; or D90 from 8 microns to 15 microns, preferably from 9 microns to 14 microns, more preferably from 9.2 microns to 13.5 microns; or D98 range from less than 28 microns, preferably from 1 micron to less than 27 microns, more preferably less than 26 microns or from 1 micron to less than 26 microns. More preferably the calcium carbonate has a particle size range at the aforementioned D50 and D90 ranges; even more preferably at the aforementioned D50, D90 and D98 ranges. Surprisingly, it is believed that having calcium carbonate at these aforementioned particle size distribution ranges may increase fluoride stability benefits. Fluoride stability may be measured as described in herein; and generally in China's National Standard Method GB8372-2008.

The term "D50" means, in particle size distribution measurements, the mass-median-diameter, considered to be the average particle size by mass. That is, the D50 is the size in microns that splits the distribution with half above and half below this diameter by mass. The term D90 similarly means the size in microns that splits 90 percent of the distribution below the D90 by mass. And the similarly term D98 means the size in microns that 98 percent of the distribution below the D98 by mass.

The particle size of calcium carbonate (as a raw material) is measured by using a laser scattering particle sizing instrument (e.g., Bettersize BT9300H from DanDong Better Instrument, China). Generally, the laser scattering technique works by measuring the light diffracted from particulates as they pass through a laser beam. Particulates scatter light at an angle that is directly related to their size. Accordingly, the Bettersize BT9300H uses the light scattering pattern associated with a sample to calculate particle size distributions. The methods of ISO 13320-1-1999 are followed. Briefly, calcium carbonate raw material is pre-dispersed in deionized water (DI-water"). And a volume of calcium carbonate slurry is transferred to sampling cell, which is filled with DI-water as dispersion solution. The particles of calcium carbonate are well dispersed by re-circulation and ultrasonication while particle size measurements are being obtained.

In one embodiment, the calcium-containing abrasive is calcium carbonate. In a preferred embodiment, the calcium-containing abrasive is selected from the group consisting of fine ground natural chalk, ground calcium carbonate, precipitated calcium carbonate, and combinations thereof. In a more preferred embodiment, the calcium-containing abrasive is selected from fine ground natural chalk, ground calcium carbonate, and combinations thereof (at the aforementioned weight percentage ranges for calcium-containing abrasives; and having the aforementioned D50, D90, and D98 measurements).

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 μm and a BET surface area of 0.5 to 3 $m^2/g$. The natural calcium carbonate may have a particle size of 325 to 800 mesh, alternatively a mess selected from 325, 400 600, 800, or combinations thereof; alternatively the particle size is from 0.1 to 30 microns, or from 0.1 to 20 microns, or from 5 to 20 microns In one embodiment, the composition of the present invention is free or substantially free of silicate.

PEG

The compositions of the present invention may comprise polyethylene glycol (PEG), of various weight percentages of the composition as well as various ranges of average molecular weights. In one aspect of the invention, the compositions have from 0.1% to 15%, preferably from 0.2% to 12%, more preferably from 0.3% to 10%, yet more preferably from 0.5% to 7%, alternatively from 1% to 5%, alternatively from 1% to 4%, alternatively from 1% to 2%, alternatively from 2% to 3%, alternatively from 4% to 5%, or combinations thereof, of PEG by weight of the composition. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula is: $H-(OCH_2CH_2)_n-OH$. One supplier of PEG is Dow Chemical Company under the brand name of CARBOWAX™.

Sweetener

The oral care compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Fluoride Ion Source

The compositions may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the composition, alternatively from about 0.005% to about 2.0% by weight of the composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, and zinc fluoride. In one embodiment the dentifrice composition contains a fluoride source selected from stannous fluoride, sodium fluoride, and mixtures thereof. In one embodiment, the fluoride ion source is sodium monofluorophosphate, and wherein the composition comprises 0.0025% to 2% of the sodium monofluorophosphate by weight of the composition, alternatively from 0.5% to 1.5%, alternatively from 0.6% to 1.7%, alternatively combinations thereof. In another embodiment, the composition comprises from 0.0025% to 2% of a fluoride ion source by weight of the composition.

pH

The pH of the dentifrice composition may be greater than pH 7.8, or from pH 8 to 13, more preferably from 9 to 12, alternatively greater than pH 8, alternatively greater than 9, alternatively from 9 to 11, alternatively from 9 to 10, or combinations thereof.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR#10010-772/Orion #8172BNWP; Epoxy body—VWR #34104-830/Orion #8165BN or VWR#10010-770/Orion #8165BNWP; Semi-micro, epoxy body—VWR #34104-837/Orion #8175BN or VWR#10010-774/Orion #3175BNWP; or (ii) Orion PerpHect combination:VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in issue, the electrode is kept immersed in a pH 7 buffer solution or an appropriate electrode storage solution.

pH Modifying Agent

The dentifrice compositions herein may include an effective amount of a pH modifying agent, alternatively wherein the pH modifying agent is a pH buffering agent. pH modifying agents, as used herein, refer to agents that can be used to adjust the pH of the dentifrice compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate), trisodium phosphate (sodium phosphate tribasic dodecahydrate or "TSP"), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid. In one embodiment, 0.01% to 3%, preferably from 0.1% to 1% of TSP by weight of the composition, and 0.001% to 2%, preferably from 0.01% to 0.3% of monosodium phosphate by weight of the composition is used. Without wishing to be bound by theory, TSP and monosodium phosphate may also have calcium ion chelating activity and therefore provide some monofluorophosphate stabilization (in those formulations containing monofluorophosphate).

Anti-Calculus Agent

The dentifrice compositions may include an effective amount of an anti-calculus agent, which in one embodiment may be present from about 0.05% to about 50%, by weight of the composition, alternatively from about 0.05% to about 25%, alternatively from about 0.1% to about 15% by weight of the composition. Non-limiting examples include those described in US 2011/0104081 A1 at paragraph 64, and those described in US 2012/0014883 A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Surfactant

The dentifrice compositions herein may include a surfactant. The surfactant may be selected from anionic, nonionic, amphoteric, zwitterionic, cationic surfactants, or mixtures thereof. The composition may include a surfactant at a level of from about 0.1% to about 10%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference. In one embodiment the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, alternatively combinations thereof, of the anionic surfactant sodium lauryl sulfate (SLS) by weight of the composition.

Thickening Agent

The dentifrice compositions herein may include one or more thickening agents. A thickening agent may be used in an amount from about 0.01% to about 15%, or from about 0.1% to about 10%, or from about 0.1% to about 5%, by weight of the composition. Non-limiting examples may include those described in US 2008/0081023 A1 at paragraphs 134 to 137, and the references cited therein.

In embodiment, the composition comprises a linear sulfated polysaccharide as a thickening agent. Carrageenans or carrageenins are one example of a linear sulfated polysaccharide. Generally, carrageenans can vary based upon the degree of sulfation that include: Kappa-carrageenan, Iota-carrageenan, and Lambda-carrageenan. Combinations of carrageenans can be used. In one embodiment, the composition contains from 0.1% to 3% a linear sulfated polysaccharides by weight of the composition, preferably from 0.5% to 2%, alternatively from 0.6% to 1.8%, alternatively combinations thereof. In one embodiment, Iota-carrageenan is used.

In one embodiment, the composition comprises a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). In one embodiment, the composition comprising from 0.5% to 5% by weight of the composition of a silica agent, preferably from 1% to 4%, alternatively from 1.5% to 3.5%, alternatively from 2% to 3%, alternatively from 2% to 5% alternatively from 1% to 3%, alternatively combinations thereof by weight of the composition.

In one embodiment, the composition comprises a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A). In one embodiment, the composition contains from 0.1% to 3% of a CMC by weight of the composition, preferably from 0.5% to 2%, alternatively from 0.6% to 1.8%, alternatively combinations thereof by weight of the composition.

In yet another embodiment, the thickener agents may comprise liner sulfated polysaccharide (e.g., carrageenans), CMC, and preferably also a thickening silica for purposes of cost savings while achieving the right balancing of viscosity and elasticity. In one embodiment, the composition comprises a thickener comprising: (a) 0.01% to less than 1.4%, preferably from 0.1% to 1.3%, more preferably from 0.5% to 1.3% of a carrageenan by weight of the dentifrice composition; and (d) greater than 0.4 wt % to 2 wt %, preferably from 0.5% to 1.8%, more preferably from 0.6% to 1.8% of a carboxymethyl cellulose (CMC) by weight of the dentifrice composition. In yet another embodiment, the aforementioned thickener further comprises 0.5% to 5%, preferably 1% to 4%, of a thickening silica by weight of the dentifrice composition.

Low or Free Humectants

The compositions herein may be substantially free or free of humectants, alternatively contain low levels of humectants. The term "humectant," for the purposes of present invention, include edible polyhydric alcohols such as glycerin, sorbitol, xylitol, butylene glycol, propylene glycol, and combinations thereof. In one embodiment, the humectant is selected from sorbitol, glycerin, and combinations thereof. In yet another embodiment, the humectant is sorbitol. In one embodiment, the composition comprises from 0% to less than 20% of humectants by weight of the composition, preferably from 0% to 10%, alternatively from 0% to 5%, alternatively from 0% to 3%, alternatively from 0% to 2%, alternatively from 0% to 1%, alternatively less than 20%, or less than 19%, 18%, 15%, 12%, 8%, 7%, 6%, 4%, 3%, 2%, 1%, or less than 0.5%; or greater than 1%, or greater than 2%, 5%, 10%, or 15%; or combinations thereof, by weight of the composition. In yet another embodiment, the composition contains less than 20% of sorbitol by weight of the composition.

In an alternative embodiment, the compositions of the present invention comprise a humectant, preferably from 1% to 15% by weight of the composition.

Colorant

The compositions herein may include a colorant. Titanium dioxide is one example of a colorant. Titanium dioxide is a white powder which adds opacity to the compositions. Titanium dioxide generally can comprise from about 0.25% to about 5%, by weight of the composition.

Flavorant

The compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

DATA

Analytical Methods

The method for assessing soluble fluoride is described consistent with the China's National Standard Method GB8372-2008. Briefly, an ion-selective electrode (ISE) is used to test soluble fluoride in dentifrice. An example of a fluoride ion meter is SARTORIUS PP-50, but an equivalent may be used. The ion meter may be fitted with a fluoride-specific ion electrode with a single-junction reference electrode by Orion Research Inc., Cat. No. 9609BNWP, but an equivalent may be used. The sample is prepared by using a balance that is accurate to the 0.0001 gram (g). 20 g of dentifrice is weighed into a tarred 50 mL plastic beaker and then gradually 50 mL of deionized water is added, while a magnetic stir bar is stirring in the plastic beaker, until the dentifrice is a completely disperse solution. The entire solution is gently transferred to a 100 mL plastic volumetric flask as to avoid generating foam (so the volume can be measured accurately), and deionized water is added to reach a total volume 100 ml, and then the solution is shaken manually to form a slurry. The formed slurry is then transferred into 10 mL centrifuge tubes, and centrifuged for 10 minutes at 15000 rotations-per-minute (RPM) (at 24149 g force) at ambient temperature. Thereafter 0.5 mL of supernatant is transferred into a 2 mL mini-centrifugal tube, and 0.7 mL of 4 mol/L HCl is added to the tub. Then the tub is capped, heated in a 50° C. water bath for 10 minutes. Thereafter the contents of the tub are transferred to a 50 mL measuring flask. The following are also added to the flask: 0.7 mL of 4 mol/L NaOH to neutralize the solution; 5 mL of citrate buffer solution (described further below); deionized water is added until a total volume of 50 mL is achieved in the flask; and then the sample solution is gently mixed. The aforementioned citrate buffer solution is prepared by dissolving 100 g of sodium citrate, 60 mL of glacial acetic acid, 60 g of NaCl, and 30 g of NaOH, all with water, adjusting the pH to 5.0~5.5, and diluting the citrate buffer solution with deionized water until a total volume of 1000 mL is achieved. Turning back to the sample solution, the entire 50 mL solution is transferred to a 50 mL plastic beaker and the fluoride level is assessed based on a fluoride standard curve using the fluoride ion meter and electrode described.

The standard fluoride curve (w/w %) is prepared by accurately measuring 0.5 mL, 1.0 mL, 1.5 mL, 2.0 mL, and 2.5 mL fluoride ion standard solutions (100 mg/kg) into five respective 50 mL plastic measuring flasks. 5 mL of citrate buffer solution (made as previously described above) into each respective flask, and then diluting each solution to the scale with deionized water. Thereafter, each solution is transferred into a 50 mL plastic beaker respectively, measuring potential E under magnetic agitation, recording potential values, and drawing E-log c (wherein "c" is a concentration) standard curve.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR#10010-772/Orion #8172BNWP; Epoxy body—VWR #34104-830/Orion #8165BN or VWR#10010-770/Orion #8165BNWP; Semi-micro, epoxy body—VWR #34104-837/Orion #8175BN or VWR#10010-774/Orion #3175BNWP; or (ii) Orion PerpHect combination:VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in issue, the electrode is kept immersed in a pH 7 buffer solution or an appropriate electrode storage solution.

FIG. 1 describes dentifrice formulations of Examples 1-15. In turn, the examples provide the data summarizes in Table 1-5 below.

Table 1 below demonstrates that the higher amount of carrageenan that is used in the described formulations of examples 1-5, the better soluble fluoride ion stability after being aged at 6 weeks at 60° C. The relatively high temperature is used to exacerbate any fluoride instability over time. Examples 1-5, as described by the formulations of FIG. 1, are briefly summarized. Examples 2-5 notable contain varying amounts of Iota-carrageenan (0.4 wt % to 2 wt %), except Control E (i.e., Example 1) which does not contain any carrageenan. Examples 1-5 contain the humectant Sorbitol at 17 wt %. Examples 1-3 contain sodium carboxymethyl cellulose while examples 4 and 5 do not. Examples 1-4 contain thickening silica while example 5 does not.

TABLE 1

| Example | Iota-Carrageenan (wt %) | Soluble Fluoride (ppm, Day 1) | Soluble Fluoride (ppm, 60° C./ 6 weeks) | Soluble Fluoride Drop (ppm, 60° C./6 weeks) |
| --- | --- | --- | --- | --- |
| 1 | 0 | 1328 | 418 | 910 |
| 2 | 0.4 | 1326 | 433 | 893 |
| 3 | 0.8 | 1348 | 637 | 711 |
| 4 | 1.3 | 1360 | 712 | 648 |
| 5 | 2 | 1345 | 818 | 527 |

Referring to Table 1 above, the lowest soluble fluoride drop on a parts per million (ppm) basis (column furthest on the right) is demonstrated by Example 5 by having 2 wt % of Iota-carrageenan having only a ppm drop value of 527. The lower the soluble fluoride ion drop, the more stable the formulation. Example 5 had the highest amount of Iota-carrageenan between the five examples and therefore demonstrated the best soluble fluoride ion stability among the five formulations. Control E (example 1) had the poorest soluble fluoride stability at 910 ppm. The increasing amount of Iota-carrageenan of examples 2, 3, and 4 (i.e., 0.4, 0.8, and 1.3 wt %, respectively) demonstrated increasing soluble fluoride ion stability as evidenced by soluble fluoride ion drop ppm values of 893, 711, and 648 respectively. In sum, Table 1 suggests the more carrageenan, the more soluble fluoride ion stable the formulation.

Table 2 below demonstrates that Lambda-carrageenan is the best between the three carrageenans in demonstrating fluoride ion stability on an equal weight basis. Examples 6-10, as described by the formulations of FIG. 1, are briefly summarized. Examples 6, 7, and 8 have increasing weight percentages (wt %) of Iota-Carrageen at 1 wt %, 2 wt %, and 3 wt %, respectively. Example 9 has Kappa-carrageenan type at 2 wt % and Example 10 at Lambda-carrageenan type at 2 wt %.

TABLE 2

| Example | Carrageenan type (% w/w) | Soluble Fluoride (ppm, Day 1) | Soluble Fluoride (ppm, 60° C./ 6 weeks) | Soluble Fluoride Drop (ppm, 60° C./6 weeks |
| --- | --- | --- | --- | --- |
| 6 | Iota/1 | 1311 | 300 | 1011 |
| 7 | Iota/2 | 1228 | 400 | 828 |
| 8 | Iota/3 | 1148 | 400 | 748 |
| 9 | Kappa/2 | 1347 | 300 | 1047 |
| 10 | Lambda/2 | 1271 | 600 | 671 |

Referring to Table 2 above, the lowest soluble fluoride drop on a ppm basis (column furthest on the right) is demonstrated by Example 10 by having 2 wt % of Lambda-carrageenan having only a ppm drop value of 671. Examples 7, 8, and 10 all have equal amounts (2 wt %) of each respective carrageenan type. Lambda-carrageenan (example 10) is the most effective for soluble fluoride ion stability, while Kappa-carrageenan (example 9) is the least effective at 1047. Notably, the increasing amount of Iota-carrageenan of examples 6, 7, and 8 respectively, show increasing amount of soluble fluoride ion stability (evidenced by the lower ppm drops of 1011, 828, and 749, respectively).

Table 3 below demonstrates that a carrageenan containing dentifrice formulation is better at fluoride ion stability than two control formulations. Examples 11, 12, and 13, as described by the formulations of FIG. 1, are briefly summarized. Example 11 contains Iota-carrageenan at 1.4 wt %. Control A (Example 11) and Control B (Example 13)

formulations do not have any carrageenan. Control A and Control B formulations both have slightly more sodium carboxymethyl cellulose (CMC) and thickening silica than Example 11, but notably Control B also has tetra sodium pyrophosphate (TSPP).

TABLE 3

| | | Soluble Fluoride drop (ppm) | | |
|---|---|---|---|---|
| Example | Formula difference: | 60° C. 4 weeks | 60° C. 6 weeks | 30° C. 52 weeks |
| 11 | Iota-carrageenan (1.4 wt %) | 530 | 830 | 330 |
| 12 | No Carrageenan Tetrasodium Pyrophosphate | 888 | 988 | 688 |
| 13 | Tetrasodium Pyrophosphate No Carrageenan | 676 | 876 | 376 |

Referring to Table 3, the data takes into account possible fluoride ion stability effects of CMC, silica, and TSP. Given the lower soluble fluoride ion drop (ppm) of carrageenan-containing Example 11 at 4 weeks and 6 weeks at 60° C., as well as 30° C. for about one year, indicates that the carrageenan is providing improved fluoride ion stability in the described formulation as compared the control formulations. Example 12 does not contain carrageenan, but does contain tetrasodium pyrophosphate (TSPP).

Table 4 below demonstrates that a pH greater than 8.0 provides better fluoride ion stability in the dentifrice formulations described herein. Examples 11, 14, and 15, as described by the formulations of FIG. 1, are briefly summarized. Example 11 is at pH 9.4 and contains 1.414 wt % of Iota-carrageenan, and also notably contains CMC and silica. Control C (Example 14) and Control D (Example 15) formulations are at a lower pH of 7.8 and 8.3, respectively. Controls C and D both also contain Iota-carrageenan at 2 wt % and 1.4 wt %, respectively. The weight percentages of silica, saccharine, and monofluorophosphate slightly of Controls C and D differ from Example 11. Compared to example 11, Control C and D also has a lower level of calcium carbonate (25 wt % vs. 42 wt %) and higher level of water (65.32 wt % v. 48.96 wt %).

TABLE 4

| Ex. | pH | Soluble Fluoride (ppm, Day 1) | Soluble Fluoride (ppm, 60° C., 4 weeks) | Soluble Fluoride Drop (ppm vs Day 1) | Soluble Fluoride drop percentage (vs Day 1) |
|---|---|---|---|---|---|
| 11 | 9.4 | 1130 | 600 | 530 | 47% |
| 14 | 7.8 | 850 | 340 | 510 | 60% |
| 15 | 8.3 | 860 | 360 | 500 | 58% |

Referring to Table 4, of the three Iota-carrageenan containing samples, Example 11 has the best fluoride ion stability effects at 4 weeks at 60° C. having the highest pH of 9.4 by having a soluble fluoride ion drop of 47% compared to Controls C and D which had much higher drop percentage at 60% and 58%, respectively. Therefore, the data suggests that pH 8.3 is better than 7.8, and pH 9.4 is better than 8.3 when it comes to fluoride ion stability.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   (a) about 45% to about 75% of water by weight of the composition;
   (b) about 25% to about 50% of a calcium-containing abrasive by weight of the composition;
   (c) about 0.0025% to about 2% of a fluoride ion source by weight of the composition;
   (d) about 1.3% to about 6% of the carrageenan by weight of the composition wherein the carrageenan is selected from the group consisting of Kappa-carrageenan, Iota-carrageenan, Lambda-carrageenan, and combinations thereof; and
   (e) pH greater than 9;
   (f) wherein the composition does not comprise thickening silica.

2. The composition of claim 1, wherein carrageenan comprises Lambda-carrageenan.

3. The composition according to claim 2, wherein the water is about 50% to about 60% by weight of the composition.

4. The composition of claim 2, wherein the composition comprises about 1.8% to about 3% carrageenan.

5. The composition according to claim 1, wherein the calcium-containing abrasive is about 27% to about 47% by weight of the composition, wherein the calcium-containing abrasive is selected from the group consisting of fine ground natural chalk, ground calcium carbonate, precipitated calcium carbonate, and combinations thereof.

6. The composition according to claim 4, wherein the calcium-containing abrasive comprises calcium carbonate.

7. The composition according to claim 1, wherein the composition further comprises about 0.1% to about 12% of a surfactant by weight of the composition, wherein the surfactant is an anionic surfactant.

8. The composition according to claim 7 wherein the anionic surfactant comprises sodium lauryl sulfate.

9. The composition according to claim 1, wherein the fluoride ion source comprises sodium monofluorophosphate.

10. The composition according to claim 8, wherein the fluoride ion source comprises sodium monofluorophosphate.

11. The composition according claim 1, wherein the composition further comprises humectant, wherein the humectant is from about 1% to about 10% by weight of the composition, wherein the humectant is selected from glycerin, sorbitol, and combinations thereof.

12. A dentifrice composition comprising:
(a) about 45% to about 75% of water by weight of the composition;
(b) about 25% to about 50% of a calcium-containing abrasive by weight of the composition;
(c) about 0.0025% to about 2% of a fluoride ion source by weight of the composition; and
(d) about 1.3% to about 7% of a Lambda-carrageenan by weight of the composition and
(e) pH greater than 9;
(f) wherein the composition does not comprise thickening silica.

13. The composition of claim 12, wherein the Lambda-carrageenan has a repeating unit of D-galactose-2-sulfate-D-galactose-2,6-disulfate providing a sulfate ester content from about 30% to about 40% by weight of the Lambda-carrageenan, wherein the Lambda-carrageenan is about 1.3% to about 6% by weight of the composition.

14. The composition of claim 12, wherein the pH is from pH 9 to pH about 12.

15. The composition of claim 12, wherein the calcium-containing abrasive comprises calcium carbonate, wherein the calcium-containing abrasive is from about 27% to about 47% by weight of the composition.

16. The composition of claim 15, wherein the calcium carbonate is selected from the group consisting of fine ground natural chalk, ground calcium carbonate, and combination thereof.

17. A method of treating tooth enamel comprising the step of brushing teeth with the dentifrice composition according to claim 1.

18. The dentifrice of claim 12 wherein the composition comprises about 1.8% to about 3% Lambda-carrageenan.

19. The dentifrice of claim 1 wherein the composition does not comprise carboxymethyl cellulose.

20. The dentifrice of claim 12 wherein the composition does not comprise carboxymethyl cellulose.

* * * * *